United States Patent [19]

Heinz

[11] 4,343,997
[45] Aug. 10, 1982

[54] COLLIMATOR ASSEMBLY FOR AN ELECTRON ACCELERATOR

[75] Inventor: Lothar Heinz, Neunkirchen, Fed. Rep. of Germany

[73] Assignee: Siemens Medical Laboratories, Inc., Walnut Creek, Calif.

[21] Appl. No.: 168,169

[22] Filed: Jul. 14, 1980

[51] Int. Cl.³ .................. A61N 5/10; G21K 1/02; H05H 7/00
[52] U.S. Cl. ................................................ 250/505.1
[58] Field of Search ............................ 250/510, 505

[56] References Cited

U.S. PATENT DOCUMENTS

| | | | |
|---|---|---|---|
| 2,998,526 | 8/1961 | Green et al. | 250/505 |
| 3,040,175 | 6/1962 | Kern . | |
| 3,407,300 | 10/1968 | Hansen . | |
| 3,539,813 | 11/1970 | Resnick . | |
| 3,781,564 | 12/1973 | Lundberg | 250/505 |
| 4,121,109 | 10/1978 | Taumann et al. . | |
| 4,157,475 | 6/1979 | Stock et al. | 250/505 |
| 4,220,866 | 9/1980 | Taumann et al. . | |

FOREIGN PATENT DOCUMENTS 3017745 11/1980 Fed. Rep. of Germany .
2379294 9/1978 France .
2406889 5/1979 France .
1110894 4/1968 United Kingdom .
1149063 4/1969 United Kingdom .

Primary Examiner—Alfred E. Smith
Assistant Examiner—T. N. Grigsby
Attorney, Agent, or Firm—Spellman, Joel & Pelton

[57] ABSTRACT

The collimator assembly comprises a collimator shielding block for blocking undesired X-rays and an insert piece inserted into the shielding block. The insert piece, which is made of a material of high atomic number, has an inner conical surface which defines the X-ray cone transmitting the insert piece and therefore the maximum field size which can be obtained for medical treatment. In order to supply different maximum field sizes, there are provided means for easily interchanging the insert in the collimator shielding block with another insert having a different interior conical dimension. By using inserts of different cone angles, which can easily be inserted into the shielding block, for instance by means of a screw thread from below the shielding block, morbid tissues of different sizes can be treated while the surrounding healthy tissue is fully protected.

6 Claims, 5 Drawing Figures

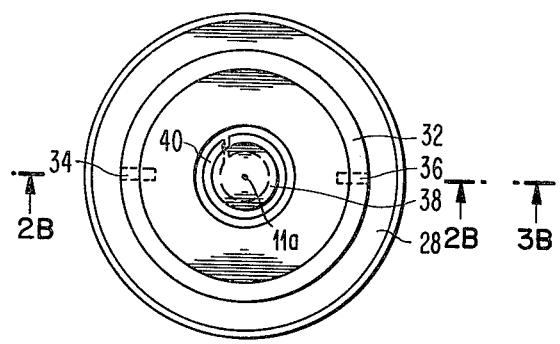
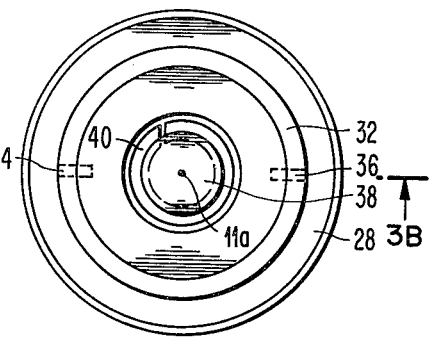
FIG. 2A  FIG. 3A
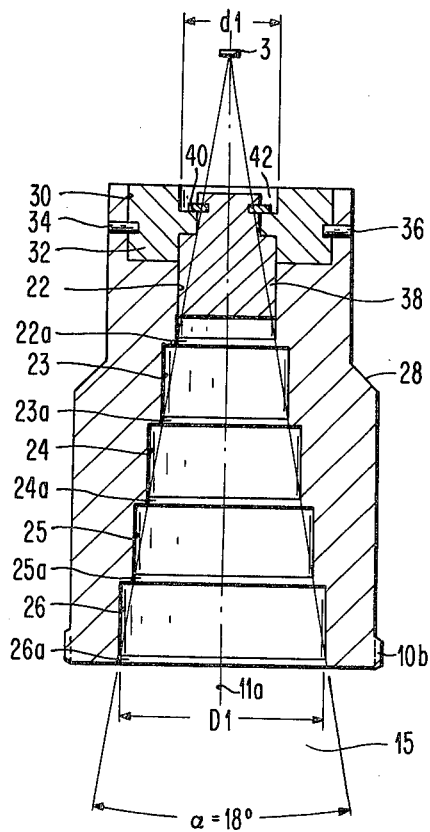
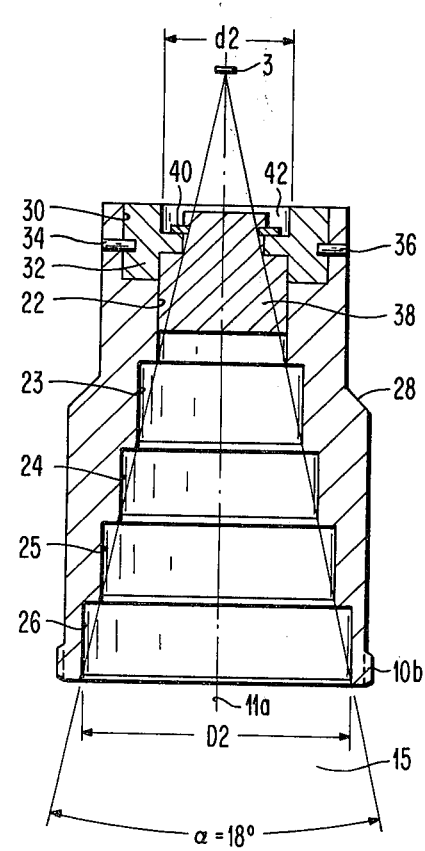
FIG. 2B  FIG. 3B

COLLIMATOR ASSEMBLY FOR AN ELECTRON ACCELERATOR

BACKGROUND OF THE INVENTION

1. Field of the Invention

This invention relates to an electron accelerator including a target exposed to the electron beam for the purpose of producing X-ray radiation and a collimator assembly limiting or defining the X-ray cone. More particularly, this invention relates to a collimator assembly for an electron accelerator, the collimator assembly comprising a collimator shielding block for blocking undesired X-rays and an insert piece or bushing inserted into the shielding block for defining the cone of the X-ray beam.

2. Description of the Pior Art

In radiation therapy, the X-ray cone issuing from an electron accelerator should have a dose rate or intensity of equal magnitude over its entire cross-section. This is necessary in order to be able to apply the minimum dose required for destroying the diseased tissue in the region of the seat of the disease, and at the same time to be able to spare the adjacent healthy tissue.

In electron accelerators the X-ray radiation is produced in a target by accelerated electrons. The dose rate in the X-ray cone being issued has a conical characteristic with a maximum in the direction in which the electron beam impinges upon the target. This maximum most often coincides with the symmetry axis of the collimator. From U.S. Pat. No. 4,157,475 it is known to obtain an equal intensity or dose rate distribution across the X-ray cone defined by the collimator assembly by installing a compensating member or flattening filter in the X-ray cone. This flattening filter has a conical construction. It is adapted in its form and in its radiation absorption properties to the characteristic of the dose rate at its point of application. Behind the flattening filter an X-ray cone is obtained having a dose rate of equal magnitude at a fixed tissue depth (for instance 10 cm) over the entire cross-section of the X-ray cone. At a lesser tissue depth (for instance 3 cm) the dose rate would increase from the interior toward the exterior, i.e. radially from the axis (non-uniform dose rate distribution). This could lead to a greater dose charge on the healthy tissue. In order to avoid the undesired excessive increase in the dose rate in the marginal region of the X-ray cone at a lesser tissue depth, it is known from U.S. Pat. No. 4,157,475 to roughen the interior wall surfaces of the collimator which limit the X-ray cone and define a conical passageway for the X-ray cone, in a direction transverse to the radiation direction. Particularly, steped grooves may be introduced into the interior wall surfaces, these grooves being arranged transversely to the radiation direction. The inner wall surfaces may be grooved such as to provide axially spaced relatively narrow annular ridge portions each conforming to the perimeter of the conical passageway and relatively wide annular intermediate wall portions providing groove regions such that the annular intermediate wall portions extend outwardly and are clear of the perimeter of the conical passageway. Each groove region may have a width dimension measured along the conical passageway which greatly exceeds the width of the annular ridge portions, but is not greater than about five millimeters. The ridge portions may have a slight pitch in the radiation direction in the manner of a screw thread. Due to the stepped grooves, there is a displacement of scatter locations to greater depths of the material. The quanta scattered at an acute angle are strongly absorbed in the edges of the grooves.

From U.S. Pat. No. 4,157,475 it is also known to admit the step-shaped grooves into a sleeve or bushing. This bushing is inserted in a fixed manner into the collimator shielding block. The bushing is not intended to be removed. The bushing consists of a material of low atomic number, such as, for example, iron, copper, or aluminum, whose atomic number is less than that of the collimator shielding block. Accordingly, the forward scattering is more pronounced in this material.

Due to the fixed bushing and in accordance with the fixed dimensions of the passageway, the collimator assembly has a certain maximum X-ray field size. Smaller fields may be obtained by means of adjustable X-ray shielding plates which are arranged behind the collimator assembly.

In medical applications tissues of various sizes are irradiated by X-rays. In such applications it seems desirable to have available a collimator assembly that allows for various maximum X-ray field sizes. Removing the total collimator assembly and replacing it by another one having different dimensions of its X-ray passageway is time consumming, tedious and expensive.

Compensating or flattening filters are known from Rev. Scient. Instr. 27, 1956, p. 584.

SUMMARY OF THE INVENTION

1. Objects

An object of this invention is to provide a collimator assembly for linear accelerator which allows for application of various X-ray field sizes without removing and/or replacing the total collimator assembly.

Another object of this invention is to provide a collimator assembly for a linear accelerator which can be easily adapted to various sizes of morbid tissues which are to be exposed to the X-ray field of the accelerator.

Still another object of this invention is to provide a collimator assembly for a linear accelerator that defines an X-ray cone having a dose rate of equal magnitude over its entire cross-section at various tissue depths of a patient, wherein the collimator assembly comprises a collimator shielding block and an insert piece or bushing which is readily inserted into said block and which may easily be machined.

Still another object of this invention is to provide a collimator assembly having interchangeable passageways, wherein the process of interchanging does not require expensive and time-consuming adjustments.

Still another object of this invention is to provide a collimator assembly having interchangeable inserts which can be used in linear accelerators of different electron energy levels.

2. Summary

According to this invention, the collimator assembly comprises a collimator shielding block for blocking undesired X-rays and a bushing inserted into the shielding block. The bushing has a conical passage opening for transmitting X-rays therethrough and for defining the X-ray cone. There are provided means for easilly interchanging the bushing in the collimator shielding block. Therefore, bushings of different cone-defining passage openings can be inserted readily into the shielding block. If a larger area is to be irradiated, a bushing will be used which has a passageway of a larger cone angle.

In a preferred embodiment having a simple configuration, there is provided a thread on the bushing and a corresponding thread in the shielding block. Thus, the bushing can be threadibly engaged with the shielding block. It can easily be replaced by another bushing having different dimensions of its passage opening.

The bushing should be made of a material having a high atomic number. Thus, the bushing is part of the X-ray shield which incorporates also the X-ray shielding block. The bushing may consist of the same material as the collimator shielding block, for instance, a material containing tungsten.

The foregoing and other objects, features and advantages of the invention will be apparent from the following more particular description of preferred embodiments of the invention, as illustrated in the accompanying drawings.

The term "bushing" is intended to mean an insert piece or insert herein.

BRIEF DESCRIPTION OF THE DRAWINGS

In the drawings:

FIGS. 2 A and 2B show a cross-section of a first interchangeable bushing or insert, which can be used in the collimator assembly illustrated in FIG. 1; and FIGS. 3A and 3B show cross-section of a second interchangeable bushing or insert, which can also be used in the collimator assembly illustrated in FIG. 1.

DETAILED DESCRIPTION OF THE PREFERRED EMBODIMENT

Figure 1:
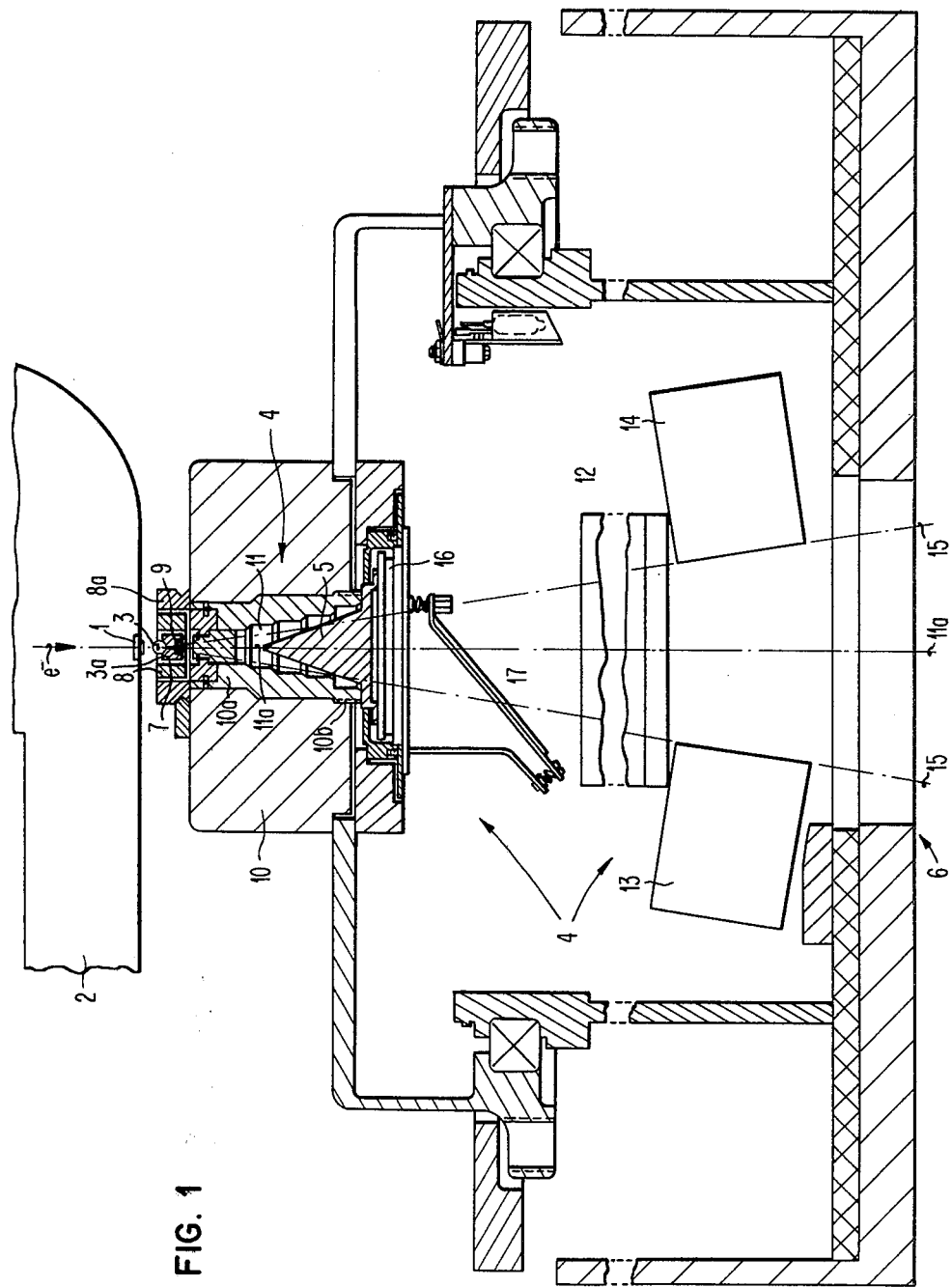
FIG. 1 is a cross-section of a beam-defining system of an electron accelerator.

FIG. 1 affords a view of the relative positions of the exit window 1 of a vacuum envelope 2, of a target 3 for generating X-rays when hit by high energy electrons e⁻, a collimator system 4, and a conical flattening filter 5, in an X-ray beam defining system 6 of an electron accelerator. The target 3 is arranged on a target body 3a in the radiation direction directly behind the exit window 1 of the vaccum envelope 2. The target 3 is mounted within a cylindrical opening or bore 7 of a carrying plate 8. The carrying plate 8 is part of a slide 8a for removing the target 3 out of the electron path. Disposed in the lower end of the target body 3a is an absorption member 9, arranged in the radiation direction behind the target 3, to absorb the remaining electrons which are not absorbed in the target 3.

The collimator system 4 is disposed in the radiation direction directly behind the carrying plate 8 of the target 3. Said collimator system 4 comprises a thick walled collimator shielding block or collimator 10, an interchangeable bushing or insert 10a which is inserted into an insert opening of the collimator 10 and which has a stepped passage opening 11, and X-ray shielding plates 12, 13 and 14 which are adjustable relative to the beam axis or iso-axis 11a. The passage opening 11 of the collimator insert 10a limits or restricts the maximum X-ray cone 15.

The insert 10a is introduced into and secured within the collimator 10 by means of corresponding threads 10b. These threads 10b are located on the lower outer part of the bushing 10a and inside the lower part of the insert opening in the collimator 10, respectively.

Between the passage opening 11 of the collimator insert 10a and the adjustable X-ray shielding plates 12, 13 and 14 is arranged an ion or X-ray dose chamber 16 for the purpose of monitoring the issued X-ray radiation and a mirror 17.

The flattening filter 5 is mounted such that it projects inwardly into the stepped passage opening 11 of the collimator insert 10a. It is centered relative to the central ray or beam axis 11a which generally corresponds to the symmetry axis of the collimator system 4. More details of the insert 10a are shown in FIGS. 2 and 3.

As can be seen in FIGS. 2 and 3, the inner wall surface of the insert 10a contains five stepped annular grooves 22, 23, 24, 25 and 26 arranged longitudinally therein. The number of grooves in the usual size collimator 10 normally used can be from four to six to achieve favorable results. Under special circumstances the number of grooves can be higher or lower. The grooves 22 to 26 have a cylindrical shape. The diameter of the grooves 22 to 26 is increased respectively from the top to the bottom of the insert 10a so as to produce a norm which is conical in cross-section.

Comparing the two inserts 10a illustrated in FIGS. 2 and 3, respectively, it may be seen that in FIG. 2 the highest groove 22 has a 8iameter d1 which is smaller than the diameter d2 of the highest groove 22 in FIG. 3, and in in FIG. 2 the lowest groove 26 has a diameter D1 which is smaller than the diameter D2 of the lowest groove 26 in FIG. 3. Thus it may be seen, the passage opening 11 of the insert 10a of FIG. 2 may form a conical angle of $\alpha = 18°$, for instance, while the passage opening 11 of FIG. 3 may have an angle of $\alpha = 25°$, as an example. The inserts 10a of FIGS. 2 and 3 are determined for different field sizes of the X-ray beam in the patient plane. For instance, the beam of FIG. 2 may have a diameter of 37 cm in the patient plane, while the beam of FIG. 3 may have a diameter of 50 cm.

The widths of the grooves 23 to 26, measured in the radiation direction of the X-rays, may be between 1 and 2 centimeters. For instance, it was found that a width of 1.4 centimeters may be chosen when five grooves 22 to 26 are selected. This value is higher than in structures formly presented.

The cylindrical grooves 22 to 26 are simple to manufacture. It should be noted that their lower edge is beveled to provide relatively narrow annular rim portions 22a to 26a, respectively. These rim portions 22a to 26a form the conical perimeter of the passageway 11. As mentioned above, due to the dimensions chosen in the illustrated embodiments, the insert 10a in FIG. 2 may have a cone angle of $\alpha = 18°$, and the insert 10a of FIG. 3 may have a cone angle of $\alpha = 25°$. The cone angle $\alpha$ determines the maximum field size of the X-ray fields. Inserts 10a may be provided. By interchanging the inserts 10a in the collimator 10, an appropriate field size may be selected.

The insert 10a consists of a material of high atomic number, such as, for example, tungsten or tungsten alloy, whose atomic number is comparable with or equal to that of the material of the collimator shielding block 10. Accordingly, the insert 10a is part of the X-ray shielding device of the linear accelerator.

Electrons e⁻ of high energy are generated by acceleration within the linear accelerator. The X-ray radiation is produced by collision of the accelerated electrons with the target 3. The X-ray radiation has a specific intensity characteristic which will be referred to as conical. Its intensity maximum coincides with the direction of the impinging electron beam. The flattening filter 5 installed in the collimator system 4 is precisely adapted with regard to its absorption value and its shape to the intensity characteristic of the X-ray radiation issuing from the target 3. Accordingly, the intensity of the X-ray beam cone 15, with the exception of the marginal regions, is flattened by the flattening filter 5 over the radiation cross-section, so that a unified intensity distribution will result. In other words, the flattening filter 5 helps to provide an X-ray beam of uniform intensity across the cross-section on a patient to be treated.

On the marginal region of the X-ray beam cone 15, the intensity would be excessively increased over an annular area of the cone cross-section at low tissue depths, if a smooth conical passage opening 11 were used. However, due to the grooves 22 to 26 disposed transversely to the radiation direction in the passage opening 11, such an intensity increase is virtually eliminated.

As can be seen in FIGS. 2 and 3, the inserts 10a have different cone angles α, yet the same outside appearance (length, diameter, etc.). They are each formed by a cylindrical piece having an upper and a lower cylindrical portion. The diameter of the upper portion is smaller than the diameter of the lower portion, thus forming a shoulder 20 midway on the outer surface. The thread 10b is located on the lower part of the lower portion. The insert 10a is inserted into the collimator 10 from below when the filter 5 and the dose chamber 16 are removed. This is an important feature of the illustrated design, since the insert 10a can thus be easily interchanged without disconnecting or moving heavy ports of the linear accelerator.

In the upper face of the insert 10a facing the target 3 is arranged a cylindrical recess 30. This recess 30 has a large diameter than the highest groove 22. Located in this recess 30 is a ring-shaped or annular piece or plug 32 which may be made of stainless steel or titanium. Generally speaking, it is made of a material of low effective cross-section for gamma/neutron processes. The thickness of this ring-shaped plug 32, measured in the radiation direction of the X-rays, may correspond to the half-value depth for X-rays. The plug 32 serves to reduce the production of undesired neutrons. It is secured in its position by two horizontal pins 34 and 36, which may be two oppositely located roll pins. In the center of the plug 32 is provided a cylindrical electron absorber 38 which may be made, for instance, of aluminum. The electron absorber 38 is stepped and inserted from below, that is from the passage opening 11. It is secured on the plug 32 by a snap ring 40. The snap ring 40 is arranged in an upper recess 42 of the plug 32. The length of the electron absorber 38 is selected according to the energy of the accelerated electrons.

As can be seen in FIGS. 2 and 3, the insert 10a along with the plug 32 and the electron absorber 38 form a interchangeable unit. Therefore, in manufacturing linear accelerators a multitude of such units can be provided, and a particular accelerator which is laid out for a specific energy level can be equipped with a specific unit which is chosen in accordance with the selected energy level. Thus, the application of inserts may facilitate the standardization of production.

While the form of the collimator assembly herein described constitutes a preferred embodiment of the invention, it is to be understood that the invention is not limited to this precise form of assembly, and that a variety of changes may be made therein without departing from the scope of the invention.

What is claimed is:

1. In an electron accelerator including a target exposed to an electron beam for the purpose of producing X-ray radiation, a collimator assembly for providing a flattened dose rate characteristic over the central region of the cross-section of the transmitted X-ray beam cone, a collimator shielding block in said collimator assembly for blocking undesired X-rays, at least two inserts comprising a material of high atomic number, one of said inserts being inserted into said collimator shielding block, each of said inserts having a stepped central opening and inner wall surfaces at the margin of the X-ray cone, said inner surfaces having annular grooves transverse to the X-ray radiation for providing a dose rate at the margin of the transmitted X-ray radiation cone which is relatively uniform and matched to the dose rate at the central region of the transmitted cone, whereby said grooves in said inner wall surfaces are cylindrical grooves, the diameter thereof increasing in the direction of said X-ray radiation, and whereby the width of said grooves in said X-ray radiation direction is between one and two centimeters, and means for easily interchanging said inserts in said collimator shielding block.

2. The collimator assembly of claim 1, wherein said inserts are made of the same material as said collimator shielding block.

3. The collimator assembly of claim 1, wherein said material comprises tungsten.

4. The collimator assembly of the claim 1, wherein said cylindrical grooves have beveled annular rims.

5. The collimator assembly of claim 1, wherein between three and seven cylindrical grooves are provided in said inner wall surfaces of said inserts.

6. An X-ray collimator assembly comprising a collimator providing a conical passageway for the transmission of an X-ray cone and a conical flattening filter centered relative to the central axis of the conical passageway such that the transmitted dose rate behind the conical flattening filter is essentially constant over the central region of the transmitted X-ray cone, said collimator having inserted an insert of a material of high atomic number with inner wall surfaces defining said conical passageway for the X-ray cone, said inner wall surfaces being grooved to provide axially spaced relatively narrow annular ridge portions each conforming to the perimeter of the conical passageway and relatively wide annular intermediate wall portions providing cylindrical groove regions such that the annular intermediate wall portions are clear of the perimeter of the conical passageway, each groove region having a width dimension as measured along the conical passageway which largely exceeds the width of the annular ridge portions and which is between one and two centimeters, said grooved inner wall surfaces serving to provide an essentially uniform dose rate at the margin of the X-ray cone matched with the dose rate at the central portion of the transmitted X-ray cone, and means for easily attaching said insert to and easily removing said insert from said collimator.

* * * * *